(12) United States Patent
Clark et al.

(10) Patent No.: US 10,835,189 B2
(45) Date of Patent: Nov. 17, 2020

(54) X-RAY IMAGING SYSTEMS AND METHODS, AND METHODS OF MANUFACTURE OF COLLIMATORS FOR USE THEREIN

(71) Applicant: ROLLS ROYCE plc, London (GB)

(72) Inventors: Daniel Clark, Belper (GB); Timothy J. Barden, Bristol (GB)

(73) Assignee: ROLLS-ROYCE PLC, London (GB)

( * ) Notice: Subject to any disclaimer, the term of this patent is extended or adjusted under 35 U.S.C. 154(b) by 0 days.

(21) Appl. No.: 16/291,039

(22) Filed: Mar. 4, 2019

(65) Prior Publication Data

US 2019/0290224 A1 Sep. 26, 2019

(30) Foreign Application Priority Data

Mar. 23, 2018 (GB) .................................. 1804679.7

(51) Int. Cl.
| | | |
|---|---|---|
| *G02B 27/30* | (2006.01) | |
| *G21K 1/02* | (2006.01) | |
| *A61B 6/03* | (2006.01) | |
| *A61B 6/00* | (2006.01) | |

(52) U.S. Cl.
CPC ............ *A61B 6/032* (2013.01); *A61B 6/5229* (2013.01); *G02B 27/30* (2013.01); *G21K 1/02* (2013.01)

(58) Field of Classification Search
CPC ........ A61B 6/032; A61B 6/5229; G21K 1/02; G02B 27/30
See application file for complete search history.

(56) References Cited

U.S. PATENT DOCUMENTS

| | | | |
|---|---|---|---|
| 5,729,585 A | 3/1998 | Pellegrino et al. | |
| 5,859,893 A | 1/1999 | Moorman et al. | |
| 5,966,424 A | 10/1999 | Liu | |
| 6,181,764 B1 | 1/2001 | Solomon et al. | |
| 2003/0235272 A1* | 12/2003 | Appleby | B29C 33/302 378/147 |
| 2005/0084072 A1 | 4/2005 | Pinchot | |

(Continued)

FOREIGN PATENT DOCUMENTS

| | | |
|---|---|---|
| GB | 2523792 | 9/2015 |
| WO | 9423458 | 10/1994 |

(Continued)

OTHER PUBLICATIONS

Great Britain search report dated Sep. 24, 2018, issued in GB Patent Application No. 1804679.7.

(Continued)

*Primary Examiner* — David P Porta
*Assistant Examiner* — Fani Boosalis
(74) *Attorney, Agent, or Firm* — Brinks Gilson & Lione

(57) ABSTRACT

Provided herein are x-ray imaging systems, methods of x-radiography, and methods of manufacture of collimators suitable for use in x-ray imaging systems and methods of x-radiography. The systems, methods and devices proposed here may assist in providing for improved magnification of x-rays in an x-ray imaging system with improved image quality compared to known systems. It may find applications in a variety of x-ray applications, for example x-ray CT (Computed Tomography) and 2D projectional radiography for e.g. non-destructing testing purposes.

12 Claims, 4 Drawing Sheets

(56) References Cited

U.S. PATENT DOCUMENTS

2005/0281701 A1 12/2005 Lynch et al.
2007/0029491 A1 2/2007 Olden et al.

FOREIGN PATENT DOCUMENTS

WO     WO 02/098624 A1    12/2002
WO     WO 2007/095241 A2    8/2007

OTHER PUBLICATIONS

Great Britain Office Action dated Mar. 29, 2019, pp. 1-8, issued in GB Patent Application No. 1804679.7, Great Britain Intellectual Property Office, Newport, South Wales, UK.

* cited by examiner

X-RAY IMAGING SYSTEMS AND METHODS, AND METHODS OF MANUFACTURE OF COLLIMATORS FOR USE THEREIN

This application is based upon and claims the benefit of priority from UK Patent Application No. GB 1804679.7, filed on 23 Mar. 2018, the entire contents of which are incorporated by reference.

BACKGROUND

Technical Field

The present disclosure relates to x-ray imaging systems, methods of x-radiography, and methods of manufacture of collimators suitable for use in x-ray imaging systems and methods of x-radiography.

Description of the Related Art

Radiography is an imaging technique using x-rays to view or otherwise examine the internal structure of an object such as, for example, a machine component for non-destructive testing purposes, or a patient's body for medical imaging purposes.

Typically, an x-ray generator or source (for example, an x-ray tube) is used to produce a beam of x-rays in a well-known manner, by heating of a cathode filament to produce an electron beam which is accelerated by a potential difference towards a positively charged anode target. Electrons striking the anode cause emission of x-rays from the target/focal spot, which are projected towards an object to be imaged. X-rays passing through the object to be imaged (in projectional radiography), or scattered from the object to be imaged (in backscatter x-ray imaging systems) are detected by a detector, and images of the internal structure of an object can be generated as a result in a well-known manner.

Geometric unsharpness is a known problem in many x-ray imaging systems, due to the fact that the x-rays typically originate from a source of finite size, rather than from a point source. It is particularly exacerbated in systems which utilise geometric magnification e.g. to assist in looking for very small inclusions in a material. There are three main factors which control the extent of geometric unsharpness of an image produced by radiography: target/focal spot size, source to object distance, and object to detector distance.

Often, source to object distance and object to detector distance are limited by external factors such as geometry of the object to be imaged. Control of focal spot/target size is therefore commonly used to minimise geometric unsharpness. By reducing the size of the focal spot, it is possible to reduce the amount of geometric unsharpness, to thus improve the visibility of fine detail in the resulting images. However, using a small spot size is often not possible, especially in high power x-ray systems. This is because high-power x-ray systems generally require use of larger focal spot sizes to effectively dissipate heat produced at the focal spot due to bombardment by electrons from the cathode. If heat is not dissipated effectively, this can cause damage to the x-ray source, for example, by melting of the target material (typically e.g. tungsten).

In some lower power imaging system systems, e.g. 225 keV systems, it is possible to focus the electron beam to achieve a smaller target/spot size, for example, down to 400 μm. In very low energy (e.g. 45 keV) systems it is possible to focus the electron beam to achieve target/spot size of 60 μm or less. However, sizes smaller than this are typically not achievable for the reasons mentioned above. Additionally, such focused source systems can suffer from problems of reduced image brightness (due to lower maximum energy), and reduced reliability (for example, requiring a shorter service interval) in comparison to typical sealed tube x-ray sources. Furthermore, the scan rate with such 'micro-focus' sources can be slow, and the systems can also be expensive and complex in comparison to typical 'unfocussed' x-ray imaging systems.

Another problem common in x-ray imaging systems is reduced contrast in the resultant image due to noise from scattered x-rays reaching the detector. This is particularly a problem for imaging of large structures (e.g. large aero engine components). One present solution is to place collimators adjacent a detector (e.g. between the object to be imaged and the detector) such that a proportion of scattered x-rays are absorbed by the collimator and do not reach the detector. However, such collimators can significantly reduce brightness of the image formed, and also do not assist in overcoming the problem of geometric sharpness. Alternatively, it is also possible to reduce scatter (and thus reduce image noise) by increasing the x-ray energy (to several MeV) and filtering out the lower energy x-rays. However, this is generally not possible in most known x-ray imaging systems without significantly decreasing the image quality due to increased geometric unsharpness, for the reasons as discussed above.

Typically, known collimators are made by drilling of a tungsten block in a suitable pattern to provide an array of holes providing ray paths through the collimator. However, such production methods have difficulty in producing collimators having complex or fine geometry, which may be useful for certain x-radiographic techniques.

Whilst some work has been done on producing collimators with complex or fine geometry using additive manufacturing processes, challenges arise where it is desired to produce very fine holes, or holes having a high aspect ratio. In particular, some problems which current methods suffer from include:

Minimum width of ligament walls greater than desired (ligament walls being internal walls between channels of the collimator), leading to reduced image brightness;
  Unsatisfactory roughness of collimator channels/ligament walls;
  Adherent, partially bonded particles within collimator channels which may obstruct ray paths; and
  Entrapped powder within collimator channels, particularly where the channel arrays are not parallel and vertical in the build orientation.

The present disclosure has been devised in light of the above considerations.

SUMMARY

In a first aspect, there is provided an X-ray imaging system comprising:
  an x-ray source;
  a collimator having a body comprising an array of channels; and
  a detector comprising an array of sensors, each sensor in the array being arranged to receive x-rays passing through a predetermined one of the channels in the array of channels;
  wherein the collimator is disposed proximal to the x-ray source and distal from the detector, such that an object imaging space is defined between the collimator and the detector.

Due to the location of the collimator being proximal to the x-ray source (e.g. adjacent the x-ray source) and distal from the detector (rather than adjacent the detector, as in some conventional x-ray imaging systems), such that an object imaging space is defined between the collimator and the detector, x-rays pass through the collimator before encountering an objected to be imaged. In other words, the collimator is disposed between the x-ray source and an object to be imaged.

In some systems the collimator may be immediately adjacent the x-ray source, such that there is no significant space between the x-ray source and the collimator. In this way, the collimator acts to provide an array of smaller 'virtual' x-ray sources from the x-ray source. Each of these 'virtual' sources illuminates a proportion of the detector, such that each sensor in the array is arranged to receive x-rays which originate from a single defined 'virtual' source.

In use, an object to be imaged is disposed in the object imaging space between the collimator and the detector. X-rays from the x-ray source pass through the collimator via channels in the collimator body, and emerge on an object imaging side of the collimator as effective 'virtual' sources. The x-rays from each virtual source then pass through an object located in the object imaging space, before being received by the detector. The acquired image data from each sensor is then collated to construct a complete image, for example using filtered back projection, or any other suitable known analytical reconstruction algorithm. It is contemplated that iterative methods may also be used. Where the object to be imaged has a known and clearly defined geometry (e.g. because it is a component part produced from a 3D CAD model), it may be possible to reduce the time for optimisation of the image by using geometric data relating to the object to be imaged in the analytical reconstruction algorithm.

By use of such 'virtual' sources, which are smaller than the 'real' x-ray source, it may be possible to reduce geometric unsharpness and allow increased magnification of the acquired image, whilst also retaining a suitably fast scanning time, and reducing risk of heat damage to the x-ray source which can occur from use of a small 'real' x-ray source. Furthermore, by allowing for use of high energy x-ray sources whilst retaining a relatively small effective spot size, it may also reduce the amount of noise due to scattering in the acquired data at the same time as retaining satisfactory magnification capability, thus providing for improved image quality.

In more general terms, the disclosed system may therefore allow for improved magnification of x-rays in an x-ray imaging system with fewer reductions in image quality compared to known systems. It may find applications in a variety of x-ray imaging methods, for example both x-ray CT (Computed Tomography) and 2D projectional radiography.

Any suitable x-ray source may be used. For example, the x-ray source may be a microfocus source, closed tube source, or linear accelerator source.

As the person skilled in the art will understand, the relative dimensions and distances between each component part of the system are not particularly limited. However, in most configurations it is anticipated that the collimator will be closer to the x-ray source than to the detector, depending on the size of the object imaging space.

The collimator body may be made of any suitably radiographically opaque material. For example, the collimator body may comprise or consist of metals (including alloys) comprising, consisting, or consisting essentially of tungsten, thorium, tantalum, depleted uranium, rhenium, platinum, iridium, osmium or any other suitable radiographically dense metal. Preferably, the collimator body comprises tungsten. More preferably, the collimator body comprises tungsten and 1-10% of Ni, Cu, Cr or Co. As discussed below in relation to the third aspect, use of such a mixture of materials to form the collimator body may be beneficial where the collimator body is to undergo a sintering step as it may reduce the sintering temperature needed.

The density of the collimator body may be in the range of 97%-100%, to help ensure adequate blocking of x-rays not travelling through one of the channels in the collimator body. In other words, the void volume within the collimator body may be from 0% to 3%. By reducing the void volume/increasing the collimator body density, it may be possible to reduce collimator dimensions whilst still providing for suitable blocking of x-rays. Additionally, greater density may provide superior mechanical properties. However, the fabrication costs may be higher for a production of a higher-density collimator body. Accordingly, an appropriate density may be selected which balances these two factors. The array of channels may be a square array (e.g. 5×5, 6×6, 7×7, 8×8, 9×9, 10×10 etc.). However, it is contemplated that for specific applications other shaped arrays may be beneficial (e.g. rectangular array, radial array, circular array, or even an irregularly-shaped array). The spacing between each channel in the array may be regular, to minimise the amount of post-processing needed to construct a complete image from the acquired image data from each sensor, although irregular channel spacing is also contemplated. The spacing between channels in the array may be approximately equal to the diameter of the channels in the array. Alternatively, wider or narrower spacing may be used, as appropriate for the desired application. The number of channels in the array is not particularly limited, and may be selected to balance improved scanning times and/or reduced geometric unsharpness, against increased difficulty of production time of the collimator.

The shape of the channels in the array may be also selected as appropriate for the desired application. They may have e.g. a circular, square, rectangular, triangular, or other suitable cross-sectional shape.

Each channel in the array of channels may have a diameter of 0.7 mm or less, for example 0.5 mm or less, or 0.1 mm or less. The channel diameter may be e.g. from 0.005 mm to 0.05 mm (between 5μ and 50 μm inclusive), or from 0.005 mm to 0.01 mm (5 μm to 10 μm inclusive). Providing a smaller channel diameter can reduce the geometric unsharpness of the imaging system, although may also reduce total brightness. Accordingly, a suitable channel diameter may be selected which balances these two factors.

The channel diameter may be defined by the diameter of a space-holding member (for example a fibre) used to form the channel during production of the collimator, as discussed below in relation to the third aspect. Accordingly, some or all of the channels may be at least partly filled with a radiographically transparent (or near-transparent) space-holding material or medium. Material here also includes e.g. composite materials. The space-holding material/medium may be formed in any suitable manner, including but not limited to additive layer manufacturing (ALM), casting, extrusion, etc. Suitable materials include e.g. poly-methyl methacrylate (PMMA), urea, ammonium hydrogen carbonate etc., optionally in combination with a binder material such as water, agar, starch, polysaccharide, citric acid, sodium hydroxide, or any other suitable binder material.

The channels in the array may diverge in a through-thickness direction of the collimator, e.g. the array of channels may be a fan-beam (diverging in one direction) or cone-beam (diverging in 2 directions) array. Alternatively, the channels may be substantially parallel in a though-thickness direction of the collimator. A through-thickness direction of the collimator is defined as a direction generally along the length of the channels. Where only a single x-ray source is used, it may be beneficial to use a collimator having a cone-beam or fan-beam array to ensure passage of a suitable amount of x-rays through peripheral regions of the array.

The length of the channels may be e.g. 15 mm, 20 mm or more, or 25 mm or more. As the channels extend through the entire collimator body from a first face of the collimator (on a source-facing side) to a second face of the collimator (on an object-facing side), the channel length is equal to the collimator depth (e.g. the distance between first and second faces of the collimator). As the skilled person readily understands, providing channels of increased length can provide improved collimation through each channel.

The detector may have an equal numbers of sensors to the number of channels of the collimator. Each sensor in the array of may predominantly or solely receive x-rays from a single channel, e.g. there may be a 1-to-1 correspondence between channels and sensors. In some arrangements, there may be slight overlap of x-ray beams emerging from neighbouring channels such that each sensor may also receive a small amount of x-radiation from channels adjacent to its predetermined corresponding channel in the array of channels.

Similarly to the channel array, the sensor array may be a square array (e.g. 5×5, 6×6, 7×7, 8×8, 9×9, 10×10 etc.). However, it is contemplated that for specific applications other shaped arrays may be beneficial (e.g. rectangular array, radial array, circular array, or even an irregularly-shaped array).

The x-ray imaging system may comprise a plurality of x-ray sources. Alternatively, it may comprise only a single x-ray source. Whilst increasing the number of x-ray sources may be beneficial to ensure full coverage of the x-ray source side of the channel array of the collimator, it may also increase the cost of the system. Accordingly, the number of x-ray sources may be selected as appropriate, balancing these two factors.

The x-ray imaging system may further comprise other components including but not limited to x-ray shields and/or filters.

In a second aspect, there is provided a method of x-radiography comprising the following steps:
 providing an x-ray source, a collimator having a body comprising an array of channels and a detector comprising an array of sensors;
 disposing the collimator proximal to the x-ray source and distal from the detector, such that an object imaging space is defined between the collimator and the detector;
 arranging each sensor in the array of sensors to receive x-rays passing through a predetermined one of the channels in the array of channels;
 disposing an object to be imaged in the object imaging space between the collimator and the detector; and
 operating the x-ray imaging apparatus to obtain x-ray image data of the object to be imaged.

In other words, the method of x-radiography comprises:
 providing an x-ray imaging system according to the first aspect;
 disposing an object to be imaged in the object imaging space; and
 operating the x-ray imaging apparatus to obtain x-ray image data of the object to be imaged.

The step of operating the x-ray imaging system to obtain x-ray image data of the object to be imaged includes generating x-rays from the x-ray source, and allowing said x-rays to pass through channels in the collimator before passing through/interacting with an object located in the object imaging space and subsequently being received by a sensor of the detector. Image data from each sensor of the detector can then be collated to construct a complete x-ray image of the object.

A system calibration routine may be employed which uses reference patterns and energy distributions to calibrate the apparatus using reference images. This can help to correct for small aberrations or local loss of sharpness.

X-ray imaging systems and methods of the first and second aspects discussed above may be used for a wide range of applications, included but not limited to: x-ray inspection of components (e.g. imaging of aero engine castings, partial or whole assemblies of an engine, or nozzle guide vanes (NGVs) for non-destructive testing purposes); and medical imaging. The imaging method may be a 2D projectional x-ray imaging method, or may be a 3D x-ray imaging method (e.g. CT scanning).

X-ray imaging systems and methods of the first and second aspects may be particularly advantageous for applications involving imaging of high density materials, which typically require a high energy (high keV) and an accordingly large spot size, which affects quality of magnification due to geometric unsharpness as discussed above.

In a third aspect there is provided a method of manufacture of a collimator comprising the steps of:
 providing a plurality of space-holding members; and
 forming a collimator body around the space-holding members such that the space-holding members define an array of channels through the collimator body.

By using a plurality of space-holding members to define an array of channels through the collimator body, may be possible to provide a collimator having complex or fine geometry, and which overcomes some or all of the other problems which currently exist with methods of manufacture of collimators having complex or fine geometries.

The step of providing a plurality of space-holding members may comprise providing multiple individual members, e.g. a plurality of fibres which constitute the space holding component, or, alternatively, a single integral body (a space-holding component) comprising a plurality of space-holding members. The precise form that the plurality of space-holding members take is not particularly limited provided that they are able to perform the function of defining an array of channels through a collimator body formed around the space-holding members. In this way, the space-holding members may be considered to form a scaffold or scaffold frame around which the collimator body is built.

In particular, the space-holding members may be formed to define an array of channels having a diameter, spacing, shape, and number of channels in the array as set out in relation to the collimator of the x-ray imaging system of the first aspect.

The step of providing a plurality of space-holding members may comprise forming the space-holding members using an additive layer manufacturing (ALM) process, e.g. fusion deposition modelling, powder bed fusion, selective laser melting etc. Where an ALM process is used, a typical layer thickness may be e.g. 20-40 microns. Alternatively, it may comprise forming the space-holding members by another suitable process such as e.g. casting, or extrusion to form fibres, a plurality of which may constitute space-holding members.

The step of providing a plurality of space-holding members may comprise forming the space-holding members from a radiographically transparent or near-transparent material. Material here also includes e.g. composite materials. Suitable materials include e.g. poly-methyl methacrylate, urea, ammonium hydrogen carbonate etc., optionally in combination with a binder material such as water, agar, starch, polysaccharide, citric acid, sodium hydroxide, or any other suitable binder material.

The method may comprise a further optional step of removing some or all of the space-holding members after the step of forming the collimator body. This may be particularly desirable where e.g. the space holding material is not sufficiently radiographically transparent. Removal of the space-holding members may be achieved by any suitable process, including e.g. dissolution of the members using a suitable solvent, leaching out, melting out (e.g. by heating the collimator body comprising the space-holding members to a temperature above the melting temperature of the material of the space holding members). Where the space-holding member material includes volatile phases, these may be decomposed during a sintering step used for densification of the collimator body.

Alternatively, in some cases it may be preferable to leave the space-holding members in place, because they can e.g. provide improved mechanical characteristics of the collimator, such as increased toughness.

The method may comprise a further step of performing laser drilling to clear and/or widen some or all of the channels in the array of channels after removal of space-holding members. This may be beneficial to ensure that the empty channels provide suitably clear ray paths, and reduce the risk of problems caused by e.g. rough channel walls, adherent partially bonded particles, or entrapped powder.

The step of forming the collimator body may include using a powder processing technique including e.g. metal injection moulding. Such processes can be cost-effective whilst provide satisfactory feature resolution. When metal injection moulding is used, a metal powder (optionally mixed with a suitable binder) may be flowed or injected around the plurality of space-holding members contained within a suitable mould.

A metal powder used in such method is not particularly limited, provided that it comprises a suitably radiographically opaque material. For example, the metal powder may comprise, consist, or consist essentially of tungsten, thorium, tantalum, depleted uranium, rhenium, platinum, iridium, osmium or any other suitable radiographically opaque metal. The powder may comprise a mixture of metal powders. Alternatively or additionally, bi-material powders such as Ni:W Cu:W, Cr:W and Co:W could be used, for example, obtained by ball-milling a mixture of tungsten and Ni/Cu/Cr/Co particles. Where a bi-material powder is used, preferably the material comprises 90-99% tungsten, and 1-10% Ni/Cu/Cr/Co. Use of a bi-material powder can facilitate sintering as the Ni/Cu/Cr/Co particles have a lower melting point than tungsten, and accordingly may diffuse more easily at lower temperatures.

Prior to any sintering step, the collimator body is in a 'green body' state. Where the green body is suitably radiopaque, it may be used without the need for further processing steps. However further processing steps may be performed to improve the mechanical properties and/or the radio-opacity of the collimator body.

For example, spark plasma sintering (SPS) or mechanical compaction may be used to enhance the density of the green body. For some geometries an SPS system or Field Assisted Sintering Technology (FAST) may provide sufficient densification of the green body without the need for furnace sintering. For other geometries, or where greater densification is needed, furnace sintering may be performed. As discussed above, the space-holding members may remain in place during any further processing steps. Alternatively, the space-holding members may be removed prior to performing such further processing steps.

Alternatively, the step of forming collimator body may include using a sol-gel process. Use of a sol-gel process may offer advantages such as higher feature resolution compared to alternative methods. Where a sol-gel process is used, a suitable sol-gel material may be cast around the plurality of space-holding members contained within a suitable mould. One example of a suitable material may include an ionic polyelectrolyte dispersant with a suspension of tungsten particles. The material may additionally be a deep eutectic solvent. A drying step may be performed to remove the solvent (liquid) phase of the sol-gel material. Optionally, there may be a chemical reaction or reduction stage, e.g. by use of a hydrogen-rich gas mixture during drying to reduce or eliminate undesirable components. For example, greases, waxes and oils can have hydrogen bonds which can interact with x-rays. Argon, hydrogen, or nitrogen ammonia containing gases or gas mixtures may be used to break down such organic phases, e.g. to compounds such as methane which may then be extracted as exhaust gas. Finally, the resulting body may be sintered to form a suitably radiopaque collimator body.

Alternatively, the collimator body may be formed using an additive manufacturing (ALM) process, e.g. fusion deposition modelling, powder bed fusion, selective laser melting etc. Such methods may offer advantages in production of collimator bodies having complex geometries.

The skilled person will be aware of a number of other suitable manufacturing processes which may be used to form a collimator body around the space-holding members. For example, it is contemplated that methods such a tape-casting may be utilised where it is desired to make a collimator having a layered structure. The step of forming the collimator body may include forming the collimator body from any suitable material or composite material, including e.g. tungsten. The collimator body may be made from a partially or totally radiopaque material. As the skilled person will understand, the precise material used may be limited by the production process chosen.

In a fourth aspect, there is provided a method of manufacture of a collimator, comprising the steps of:
providing a plurality of foil layers, each having an array of holes; and
stacking and bonding the foil layers to form a laminated collimator body comprising an array of channels defined by aligned holes in each foil layer.

The step of bonding the foil layers may be performed by any suitable method. For example, the foil layers may be bonded using a pulsed laser to selectively braze the layers together. Alternatively, the layers may be bonded using a suitable adhesive, or mechanically held together using e.g. a clamping arrangement.

The foil layers may be formed of any suitably radiographically opaque material. For example, the foil layers may comprise metals (including alloys) comprising, consisting or consisting essentially of tungsten, thorium, tantalum, depleted uranium, rhenium, platinum, iridium, osmium or any other suitable radiographically dense metal. Preferably, the foil layers comprise or consist of tungsten.

There may be a step of providing one or more interlayers between each of the foil layers. For example, interlayers of copper, niobium, nickel or vanadium may be provided.

Optionally, there may be a further consolidation step including applying high temperatures and/or pressures to the bonded layers. The example temperature and/or pressure is not particularly limited, and may be selected as appropriate given the composition of the foil layers and (where appropriate) interlayers. The temperature and/or pressure may be selected so as to promote solid state diffusion between layers for enhanced bonding. For example, suitable consolidation conditions may be: temperature 700° C. (preferably 1000° C.) and pressure 100 MPa, for a time of 1 hour, e.g. 2-4 hours.

The method may comprise an additional step of forming an array of holes in a plurality of foil layers. The step of forming the holes may include forming the holes by any suitable method, including but not limited to: mechanical perforation (punching), etching, laser ablation etc.

Prior to stacking the layers, there may be an additional step of trimming and/or aligning the layers. Each of the layers may be trimmed to the same size, and aligned via their outer edges, before being assembled to form the laminated collimator body.

Each of the foil layers may have an identical array of holes, for example, where it is desired to produce a collimator having an array of parallel channels. Alternatively, some or all of the foil layers may have a different array of holes. For example, where it is desired to produce a collimator having a cone-beam array of channels (diverging in 2 directions), each subsequent foil layer in the laminated collimator body may have an array of holes with a spacing larger than the previous foil layer in the laminated collimator body. In this way, the holes in each layer will be slightly mismatched so that on stacking of the layers, the holes align ('align' including at least partial overlap of a hole in one layer with a hole in another layer), to define an array of diverging channels through the laminated collimator body.

The number, size, shape, spacing and arrangement of holes in each layer is not particularly limited, and may be selected as required to produce any channel configuration in the laminated collimator body as described in relation to the collimator of the x-ray imaging apparatus of the first aspect, above.

For example, some or all of the layers may have a square array (e.g. 5×5, 6×6, 7×7, 8×8, 9×9, 10×10 etc.) of holes. However, it is contemplated that for specific applications other shaped arrays may be beneficial (e.g. rectangular array, circular array, or even an irregular array).

The shape of the holes may be e.g. a circular, square, rectangular, triangular, or any other suitable shape. The diameter of the holes may be from 5 µm to 100 µm. The shape and/or size of each hole in the array of holes of a specified layer may be the same, or the array of holes in a specified layer may comprise holes having different shapes and/or sizes.

The thickness of each layer is not particularly limited, and may be determined by commercially available foil thicknesses. At present, it is possible to obtain suitable foils having a thickness as low as e.g. 3 µm. As the skilled person will understand, increasing the thickness of each foil layer may increase the internal roughness of channels in the laminated collimator body which are defined by aligned holes. This may particularly be the case in embodiments where the holes are aligned in such a way that they do not fully overlap (e.g. such as in the diverging channel example discussed above). However, working with very thin foil layers can increase the complexity of assembling the laminated collimator body and/or increase risk of damage to the foils during the assembly process. Accordingly, the thickness of the foil may be selected as appropriate to balance these two factors. The foil thickness may therefore be between 1 and 50 µm, for example the foil thickness may be 5 µm, 10 µm, 15 µm, 20 µm or 50 µm.

The method of manufacture may further comprise the step of at least partly filling some or all of the channels in the array of channels of the laminated collimator body with a radiographically transparent (or near-transparent) space-holding material or medium. For example, a space-holding material or medium may be flowed or pressed into some or all of the channels of the laminated collimator body. Material here also includes e.g. composite materials. Suitable materials include e.g. poly(methyl methacrylate), urea, ammonium hydrogen carbonate etc., optionally in combination with a binder material such as water, agar, starch, polysaccharide, citric acid, sodium hydroxide, or any other suitable binder material.

At least partly filling some or all of the channels of the laminated collimator body may provide advantages such as reduced shrinkage or compaction of the collimator body in use. Additionally, the mechanical properties of the collimator body may be improved.

The present disclosure includes the combination of the aspects and optional features described except where such a combination is clearly impermissible or expressly avoided. In particular, collimators produced using methods of manufacture as set out in the third and fourth aspects may be suitable for use in an x-ray imaging apparatus according to the first aspect or a method of x-radiography according to the second aspect. In this way, optional features set out in relation to the collimator of the x-ray imaging apparatus of the first aspect are also applicable to collimators produced using the methods of manufacture of the third and fourth aspects.

DESCRIPTION OF THE DRAWINGS

Embodiments of the present disclosure will now be described by way of example with reference to the accompanying drawings in which.

DETAILED DESCRIPTION

Figure 1:
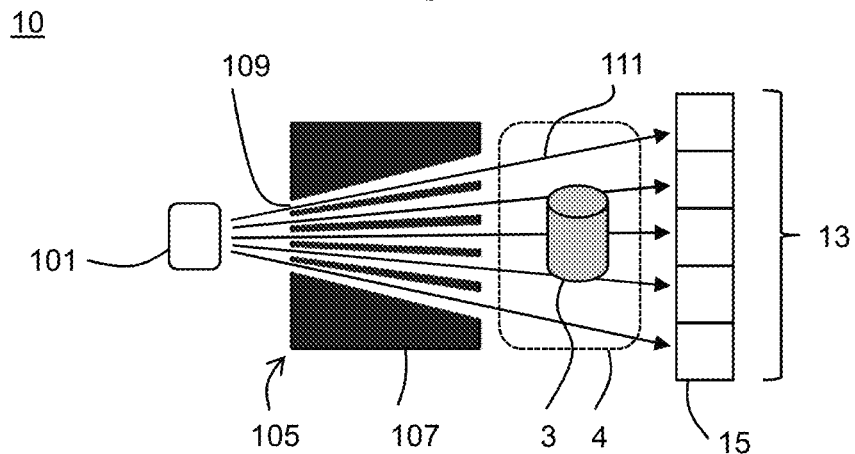
FIG. 1 shows a schematic diagram of a first x-ray imaging system.

FIG. 1 shows a schematic cross-section of a first x-ray imaging system 10 including a single x-ray source 101 (e.g. an x-ray tube), a collimator 105 and a detector 13 comprising a plurality of sensors 15. The collimator 105 is disposed adjacent to the x-ray source such that in use, x-rays from the x-ray source encounter the collimator before encountering an object 3 (located within object imaging space 4) to be imaged. In other words, the collimator 105 is disposed proximal the x-ray source 101 and distal the detector 13 such that an object imaging space 4 is defined between the collimator and the detector, in which an object 3 to be imaged can be located.

The collimator 105 comprises a collimator body 107 consisting of tungsten with a density of 97-100%. Accordingly, the collimator body is suitably radiographically opaque such that x-rays are substantially blocked by the material of the collimator body 107. The collimator body comprises an array of channels 109 which extend through the entire thickness of the collimator body, and which define a corresponding array of ray paths 111 through the collimator body. Here, the channels are unfilled holes. The array of channels diverges in a through-thickness direction so that the ray paths form a cone-beam array. Providing a cone-beam array can help to ensure adequate brightness of the final image whilst using only a single x-ray source, as the source is able to cover the full height of the channel array on the x-ray source side of the collimator.

An example arrangement such as that shown in FIG. 1 could comprise e.g. a 1 MeV x-ray source having a 10 mm focal spot, a collimator having a 64×64 cone-beam array of channels (to allow for beam spread), each channel having a diameter of 0.2 mm, and a corresponding 64×64 detector, each sensor in the detector arranged to primarily receive x-rays originating from a different channel of the collimator (e.g. channels in the collimator being in a 1-to-1 relationship with sensors in the detector). In this way, the effective source size is reduced by over an order of magnitude, from 10 mm to 0.2 mm, thus allowing for reduced geometric unsharpness, whilst allowing use of a suitably large 'real' x-ray source to enable effective heat dissipation.

Figure 2:
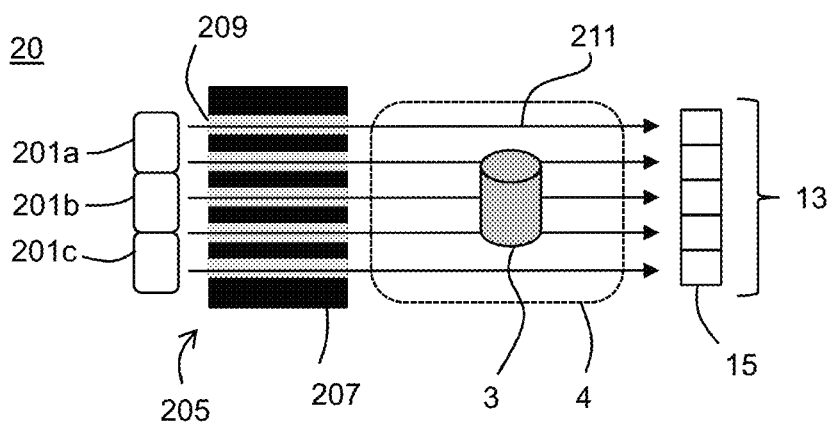
FIG. 2 shows a schematic diagram of a second x-ray imaging system.

FIG. 2 shows a schematic cross-section of a second x-ray imaging system 20 including a plurality of x-ray sources 201a,b,c, collimator 207 and detector 13 comprising a plurality of sensors 15, arranged for imaging of an object 3. The arrangement is broadly similar to that shown in FIG. 1, however, one key difference is that here, the collimator comprises an array of channels 209 which are parallel in a through-thickness direction. Accordingly, multiple x-ray sources 201a, b, c are used to ensure coverage of the full height of the channel array on the x-ray source side of the collimator. Such an arrangement has advantages in terms of ease of manufacture of the collimator (in comparison to the cone-beam collimator of the system of FIG. 1), however use of multiple sources can increase the overall cost of the system.

In the collimator 209 of FIG. 2, the channels are filled with a radiographically transparent material. This means that the channels allow passage of x-rays, whilst providing such advantages as improved durability of the collimator, and reduced risk of occlusion of the channels e.g. by dust/dirt.

The imaging arrangements shown in both FIG. 1 and FIG. 2 both comprise a detector 13 comprising an array of sensors 15. Each sensor in the detector is arranged to receive x-rays passing through a predefined channel of the collimator. In both arrangements, it can be seen that there are equal numbers of sensors and channels, so that there is 1-to-1 correspondence between channels and sensors. In this way, each sensor is arranged to primarily receive x-rays passing through a single channels, although, as will be discussed below in relation to FIG. 3, there may be some overlap of beams from adjacent channels.

The image can then be reconstructed from signal received at each sensor in the detector, for example using filtered back projection, a known analytical reconstruction algorithm. Other known iterative methods may also be used. Where the object to be imaged has a known and clearly defined geometry (e.g. because it is a component part produced from a 3D CAD model), it may be possible to reduce the time for optimisation of the image by inputting geometric data relating to the object to be imaged.

Because the collimator is disposed between the x-ray source and the object to be imaged, each channels effectively acts as a smaller (in comparison to the x-ray source) 'virtual source' of x-rays. As will be readily understood by the skilled person, by providing smaller sources, geometric unsharpness is reduced in comparison to an image obtained using the same x-ray source but without use of the above collimator/detector. This effect is particularly apparent when the channels diameter is an order of magnitude small than the actual source size (e.g. a source size of 10 mm and a collimator channel size of 1 mm or less). Additionally, because the 'real' source remains large, problems typically associated with use of small x-ray sources (e.g. poor heat dissipation, slow scan times etc.) are overcome.

Figure 3:
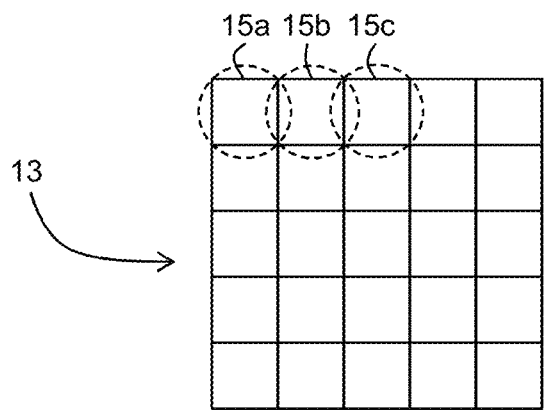
FIG. 3 shows a schematic diagram of a detector.

FIG. 3 shows a schematic diagram of a detector 13 as shown in the arrangements of FIGS. 1 and 2. The detector comprises an array of sensors 15a, b, c, etc. in a 5×5 array, to correspond to the 5×5 array of channels in the collimators 107, 207. Dotted lines represent x-ray beam footprints, each beam from a defined collimator channel. Each sensor in the detector is arranged to predominantly receive x-rays from a single channel of the collimator, e.g. it is arranged to predominantly receive a single beam of x-rays. However, here there is some overlap between x-ray beams from adjacent channels, such that each sensor receives x-rays from multiple adjacent channels. In constructing the final image from acquired image data from each sensor in the detector, this beam interference is compensated for by suitable known signal manipulation techniques.

Figure 4A:
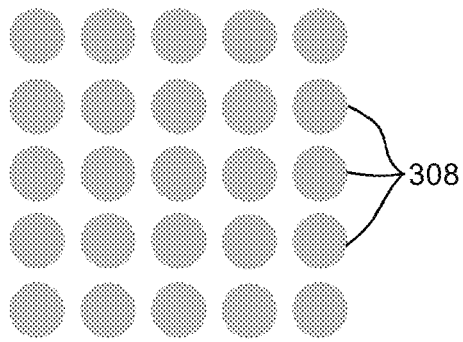
FIGS. 4a, b, and c schematically show various stages in a method of manufacture of a collimator.
Figure 4B:
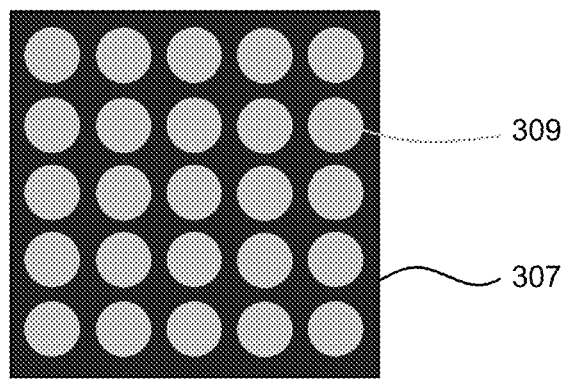
Figure 4C:
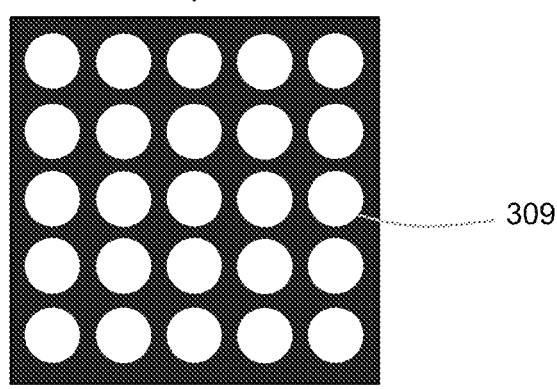

FIGS. 4a, b, and c schematically show various stages in a method of manufacture of a collimator, as a cross-section perpendicular to the through-thickness direction of the collimator. First, a plurality of space-holding members 308 are formed, e.g. by an additive layer manufacture process, in a suitable array corresponding to a desired array of ray paths. Here, each member comprises a cylindrical rod. A collimator body 307 is then formed around the space-holding members 308 using a suitable manufacturing process (e.g. metal injection moulding using tungsten powder). Each of the space-holding members defines an individual (filled) channel 309 through the collimator body. Once the collimator body has been formed, the plurality of space-holding members are then removed, leaving the array of (unfilled) channels 309 through the collimator body.

Figure 5A:
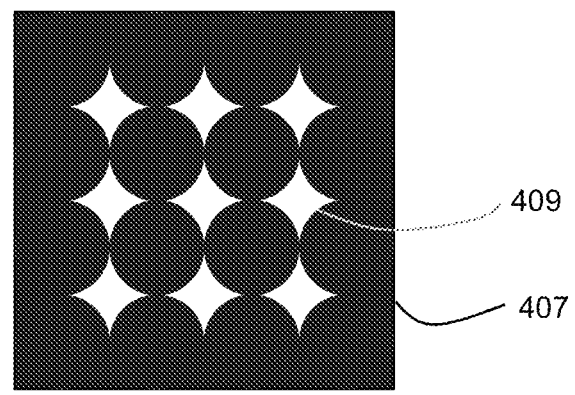
FIGS. 5a, b and c show example channel arrangements within a collimator.
Figure 5B:
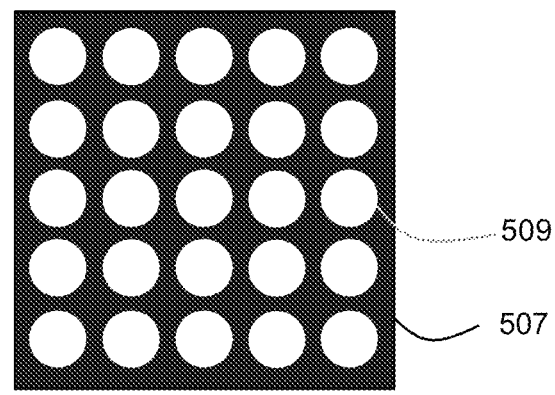
Figure 5C:
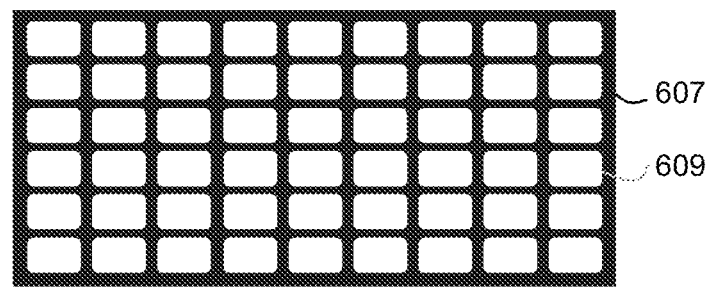

FIGS. 5a, b and c show various examples of possible channel arrangements within a collimator. Such arrangements are possible in collimators produced using both the third and fourth aspects of the present disclosure. The arrangement shown in FIG. 5a includes irregularly shaped channels 409 in a square (3×3) array through collimator body 407. The arrangement shown in FIG. 5b includes channels 509 having a circular cross-section in a square (5×5) array through collimator body 507. The arrangement shown in FIG. 5c includes channels 609 having a rectangular cross-section in a rectangular (6×9) array through collimator body 607. The aspect ratio of the rectangular channels is approximately 2:3.

Figure 6:
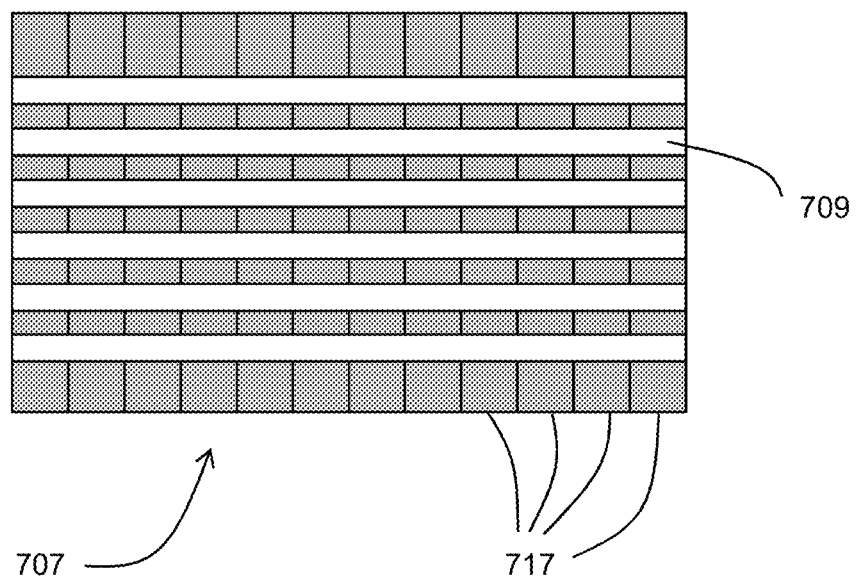
FIG. 6 shows a schematic cross-sectional view of a laminated collimator body.

FIG. 6 shows a schematic cross-sectional view of a laminated collimator body 707. The collimator body is produced by providing a plurality of foil layers 717, each having an array of holes, and stacking and bonding the foil layers to form a laminated collimator body comprising an array of channels 709 defined by aligned holes of each foil layer. Here, each foil layer comprises an identical array of holes, with the result that the aligned holes form an array of straight, parallel channels 709 passing through the laminated collimator body.

Example 2D X-Ray Applications

One example application for x-ray imaging is imaging of large aero-engine castings such as an intercase of approximately 800 mm diameter by 250 mm deep.

Current industry standard for imaging such components is a closed tube x-ray source (300 to 600 keV), having a 300 μm or greater spot size. By using x-ray imaging systems and/or methods as described herein, it is possible to reduce effective spot size down to e.g. 0.1 mm, and thus allow improved magnification and image resolution.

Another example application is imaging of partial or whole assemblies of an engine. Currently whole engine radiography is carried out using a linear accelerator source (>1 MeV), with a large spot size of e.g. 1 to 5 mm. By using x-ray imaging systems as described herein, it is possible to reduce the equivalent spot size to e.g. between 0.1 mm and 0.5 mm. Reduction in effective spot size by an order of magnitude can allowing for far greater magnification without geometric unsharpness, and can thus improve ability to measure internal features of the engine or engine assembly.

Example 3-D (CT) X-Ray Applications

Another example of a target application is 3D imaging of a nozzle guide vane (NGV). Nozzle guide vanes are typically manufactured from dense metal (e.g. nickel based superalloy), and typically have an overall size of approximately 75 mm×75 mm×75 mm, a thickness of 20-30 mm, and one or more internal passageways of the scale of 1 mm diameter. Successful imaging of the internal cooling passageway(s) in the NGV requires high image resolution due to the small size of the passageways.

Current industry standard for imaging such components is to use:

a) 450 keV source, micro-focussed to a 60 μm spot size; or b) Closed tube 450 keV source with a 300 μm spot size, (sealed system)

However, using x-ray imaging systems and methods as described herein it is possible to achieve spot sizes as low as 5-10 μm for both micro-focus and closed tube sources, whilst allowing use of high amperage x-ray sources which may enable reduced data acquisition time.

Another example application is 3D imaging of a metal casting or additive manufactured component of high geometric complexity, manufactured of a dense material (e.g. Nickel super alloy or Titanium alloy), having a size of approximately 150×150×100 mm, with 50 to 100 mm metal path (total length of metal the x-ray beam needs to penetrate), and internal features of the scale of 1 mm. Such a part requires a high resolution scan to measure features such as: small-scale internal features; surface roughness not accessible by mechanic measurement devices; and detection of material defects.

Presently, high energy (>800 KeV) x-ray sources (closed tube or linear accelerator sources) with a spot size of 1 mm or greater are used to image such parts. Such sources, as discussed above, do not allow for high magnification x-ray CT without signification geometric unsharpness.

By using x-ray imaging systems and/or methods as described herein, it is possible to reduce the spot size of such high energy sources and allow the required magnification for satisfactory imaging of such components.

Furthermore, because the disclosed systems allows use of high energy sources (to several MeV) whilst retaining a satisfactory magnification capability and resolution, It will be understood that the disclosed systems are not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

The invention claimed is:

1. An x-ray imaging system comprising:
   an x-ray source;
   a laminated collimator having a body comprising a plurality of foil layers and an array of channels through the foil layers, wherein the collimator body is suitably radiographically opaque such that x-rays are substantially blocked by a material of the collimator body and the channels are filled with a radiographically transparent material; and
   a detector comprising an array of sensors, each sensor in the array of sensors being arranged to receive x-rays passing through a predetermined one of the channels in the array of channels;
   wherein the laminated collimator is disposed proximal to the x-ray source and distal from the detector, such that an object imaging space is defined between the laminated collimator and the detector.

2. The x-ray imaging system according to claim 1 wherein there are equal numbers of sensors and channels and each sensor is arranged to receive x-rays passing through the predetermined one of the channels.

3. The x-ray imaging system according to claim 1 wherein the channels diverge in a through-thickness direction.

4. The x-ray imaging system according to claim 1 wherein the channels are substantially parallel in a through-thickness direction.

5. The x-ray imaging system according to claim 4 comprising a plurality of x-ray sources.

6. The x-ray imaging system according to claim 1 wherein each channel has a diameter of 0.7 mm or less.

7. A method of x-radiography comprising the steps of:
   providing an x-ray imaging system according to claim 1;
   disposing an object to be imaged in the object imaging space; and
   operating the x-ray imaging system to obtain x-ray image data of the object.

8. A method of manufacture of a laminated collimator, comprising:
   providing a plurality of foil layers, each having an array of holes;
   stacking and bonding the foil layers to form a laminated collimator body comprising an array of channels defined by aligned holes of each foil layer; and
   providing the laminated collimator body in an imaging system.

9. The method of manufacture of the laminated collimator according to claim 8 wherein the step of bonding the foil layers comprises:
   (i) selectively brazing the foil layers together;

(ii) bonding the foil layers using a suitable adhesive; or
(iii) mechanically bonding the foil layers in a clamping arrangement.

10. The method of manufacture according to claim 8 including the step of providing one or more interlayers between each of the foil layers.

11. The method of manufacture according to claim 8 further comprising a consolidation step of heating the laminated collimator body at a temperature $\geq 700°$ C. and pressure of $\geq 100$ MPa, for a time of $\geq 1$ hour.

12. The method of manufacture of the laminated collimator according to claim 8 further comprising the step of at least partly filling some or all of the channels in the array of channels with a radiographically transparent space-holding material.

* * * * *